US012685714B2

(12) United States Patent
Minrovic et al.

(10) Patent No.: US 12,685,714 B2
(45) **Date of Patent: *Jul. 21, 2026**

(54) MICROSPHERE FORMULATIONS COMPRISING KETAMINE AND METHODS FOR MAKING AND USING THE SAME

(71) Applicant: Oakwood Laboratories, LLC, Oakwood Village, OH (US)

(72) Inventors: Rachel Minrovic, Willoughby, OH (US); Tracy Richey, Kent, OH (US); Michaela Giltner, Akron, OH (US)

(73) Assignee: Oakwood Laboratories, LLC, Oakwood Village, OH (US)

( * ) Notice: Subject to any disclaimer, the term of this patent is extended or adjusted under 35 U.S.C. 154(b) by 374 days.

This patent is subject to a terminal disclaimer.

(21) Appl. No.: 18/151,928

(22) Filed: Jan. 9, 2023

(65) Prior Publication Data

US 2023/0225993 A1 Jul. 20, 2023

Related U.S. Application Data

(63) Continuation-in-part of application No. 17/404,128, filed on Aug. 17, 2021, now Pat. No. 12,233,165.

(60) Provisional application No. 63/297,439, filed on Jan. 7, 2022, provisional application No. 63/149,911, filed on Feb. 16, 2021, provisional application No. 63/067,068, filed on Aug. 18, 2020.

(51) Int. Cl.
*A61K 31/135* (2006.01)
*A61K 9/16* (2006.01)

(52) U.S. Cl.
CPC .......... *A61K 31/135* (2013.01); *A61K 9/1647* (2013.01)

(58) Field of Classification Search
None
See application file for complete search history.

(56) References Cited

U.S. PATENT DOCUMENTS

| | | | |
|---|---|---|---|
| 4,459,245 | A | 7/1984 | Ryon et al. |
| 5,945,126 | A | 8/1999 | Thanoo et al. |
| 6,171,078 | B1 | 1/2001 | Reto |
| 6,291,013 | B1 | 9/2001 | Gibson et al. |
| 6,479,007 | B1 | 11/2002 | Greenberg et al. |
| 10,973,780 | B2 | 4/2021 | Becker et al. |
| 2005/0025630 | A1 | 2/2005 | Ayre et al. |
| 2005/0260272 | A1 | 11/2005 | Figueiredo et al. |
| 2007/0077155 | A1 | 4/2007 | Shah et al. |
| 2011/0027331 | A1 | 2/2011 | Hobot |
| 2011/0160340 | A1 | 6/2011 | Hester et al. |
| 2011/0204533 | A1 | 8/2011 | Winchester et al. |
| 2013/0236573 | A1 | 9/2013 | Singh et al. |
| 2014/0367003 | A1 | 12/2014 | Willliamson |
| 2015/0250719 | A1 | 9/2015 | Meyer |
| 2018/0326080 | A1 | 11/2018 | Deng et al. |
| 2021/0361578 | A1 | 11/2021 | Salem et al. |

FOREIGN PATENT DOCUMENTS

| | | | |
|---|---|---|---|
| JP | 62201816 | | 9/1987 |
| JP | 2002020269 | A1 | 4/2005 |
| WO | 0110414 | A1 | 2/2001 |
| WO | 2001010414 | A1 | 2/2001 |
| WO | 02089767 | A1 | 11/2002 |
| WO | 2005107706 | A2 | 11/2005 |
| WO | 2006/120945 | A1 | 11/2006 |
| WO | 2007082061 | A2 | 7/2007 |
| WO | 2013119183 | A1 | 8/2013 |
| WO | 2019054948 | A1 | 3/2019 |
| WO | 2019126108 | | 6/2019 |
| WO | 2021108801 | A2 | 6/2021 |
| WO | 2021121366 | A1 | 6/2021 |

OTHER PUBLICATIONS

Han et al. (Pharmaceutics , 10, 264, 1-14) Formulation of Bioerodible Ketamine Microparticles as an Analgesic Adjuvant Treatment Produced by Supercritical Fluid Polymer Encapsulation (Year: 2018).*
Uchida et al. (J Microencapsul, 13(2):219-228, only abstract provided). Preparation and characterization of polylactic acid microspheres containing water-soluble dyes using a novel w/o/w emulsion solvent evaporation method (Year: 1996).*
International Preliminary Report on Patentability issued in PCT/US23/60315, dated Jun. 20, 2024 (9 pages).
United States Patent and Trademark Office, Non-Final Rejection issued in U.S. Appl. No. 17/404,128, dated Feb. 29, 2024 (13 pages).
United States Patent and Trademark Office, Final Rejection issued in U.S. Appl. No. 17/404,128, dated Jun. 21, 2024 (20 pages).
Extended European Search Report issued in EP App. No. 20835433.2, dated Jul. 24, 2023.
China National Intellectual Property Administration, First Office Action issued in Chinese Patent Application No. 202180050934.4, dated Nov. 9, 2024 (3 pages).
International Preliminary Report on Patentability issued in PCT/US2021/046220, mailing date Feb. 16, 2023.
International Search Report and Written Opinion issued in PCT/US2021/046220, mailing date Jan. 5, 2022.
Zhu et al., "Bioerodable Ketamine-Loaded Microparticles Fabricated Using Dissolvable Hydrogel Template Technology", Journal of Pharmaceutical Sciences, 108 (2019) 1220-1226.
Han et al., "Formulation of Bioerodible Ketamine Microparticles as an Analgesic Adjuvant Treatment Produced by Supercritical Fluid Polymer Encapsulation", Pharmaceutics, 2018, 10, 264.
Hirano et al., "Ketamine nano-delivery based on poly-lactic-co-glycolic acid (PLGA) nanoparticles" Applied Nanoscience, vol. 8, Apr. 11, 2018.

(Continued)

*Primary Examiner* — Tigabu Kassa
(74) *Attorney, Agent, or Firm* — Benjamen E. Kern; Kern Kendrick Pribisich

(57) ABSTRACT

Extended-release injectable microsphere formulations comprising ketamine are provided. Methods for making and using the microsphere formulations are also provided.

10 Claims, 4 Drawing Sheets

(56) References Cited

OTHER PUBLICATIONS

Han, et al., "Novel Polymeric Bioerodable Microparticles for Prolonged-Release Intrathecal Delivery of Analgesic Agents of Relief of Intractable Cancer-Related Pain", Journal of Pharmaceutical Sciences 104:2334-2344, 2015.
International Search Report and Written Opinion issued in PCT/US23/60315, mailing date Jul. 13, 2023.
First Office Action issued in CN202180050934.4 on Dec. 4, 2024.
Extended European Search Report issued in EP21858931.5 on Sep. 26, 2024.
Notice of Deficiencies issued in IL300547 on Apr. 16, 2026.
Mandal et al., "Efficacy of ketamine therapy in the treatment of depression," Indian Journal of Psychiatry, 480-485, 2019.
Second Written Opinion issued in SG11202300977S on Oct. 8, 2025.
First Written Opinion issued in SG11202300977S on Feb. 12, 2025.
Office Action issued in JP2023-511830 on Jul. 22, 2025.
Uchida et al J. Microencapsul Mar.-Apr. 1996;13(2): 219-228.
Taiwan Intellectual Property Office, First Office Action issued in Taiwanese Patent Application No. 110130523, dated Apr. 25, 2025 (5 pages).

* cited by examiner

MICROSPHERE FORMULATIONS COMPRISING KETAMINE AND METHODS FOR MAKING AND USING THE SAME

CROSS-REFERENCE TO RELATED APPLICATIONS

This application claims priority from U.S. Provisional Patent Application No. 63/297,439, filed on Jan. 7, 2022. This application is also a continuation-in-part of U.S. Nonprovisional patent application Ser. No. 17/404,128, filed on Aug. 17, 2021, and now issued as U.S. Pat. No. 12,233, 165B2, which claims priority from U.S. Provisional Patent Application No. 63/067,068, filed on Aug. 18, 2020, and U.S. Provisional Patent Application No. 63/149,911, filed on Feb. 17, 2021. Each of these applications is incorporated by reference herein in its entirety.

BACKGROUND

Ketamine (chemical formula $C_{13}H_{16}ClNO$, IUPAC name 2-(2-chlorophenyl)-2-(methylamino)cyclohexan-1-one), characterized by the general structure:

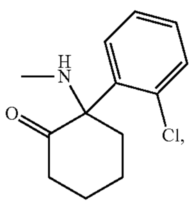 [SMILES: CNC1(c2ccccc2Cl)CCCCC1=O]

is an N-methyl-D-aspartate ("NMDA") receptor antagonist. Ketamine can be an effective analgesic. What is needed is an extended release (e.g., 1-3 days) formulation comprising ketamine for treating pain, including, for example, post-operative pain.

SUMMARY

Microsphere formulations comprising ketamine are provided. The microsphere formulations comprise polymer microspheres, each polymer microsphere comprising: (i) an active pharmaceutical ingredient ("API") comprising, consisting essentially of, or consisting of ketamine; and (ii) a biodegradable polymer comprising, consisting essentially of, or consisting of an acid end-capped poly(lactide) (a "PLA") polymer or an acid end-capped poly(D,L-lactide-co-glycolide) (a "PLGA") polymer, wherein the biodegradable polymer has an inherent viscosity (an "IV") of about 0.1 to about 0.3 dL/g. Each polymer microsphere may comprise a drug load of between about 20 wt/wt % to about 50 wt/wt %, and the polymer microspheres may have an average particle size of between about 30 μm to about 90 μm ($D_{50}$). In some aspects, the polymer microspheres are characterized by a plurality of internal emulsions, each emulsion comprising water and a surfactant. In some aspects, the polymer microspheres may be subjected to dehydration, in which case the polymer microspheres are characterized by a plurality of internal macrovoids.

In some aspects, the polymer microspheres are double emulsified. A method for making double emulsified polymer microspheres is provided, the method comprising: (i) contacting ketamine with a biodegradable PLA or PLGA polymer in the presence of a solvent to form an organic component and providing the organic component to a first homogenizer; (ii) providing an inner aqueous component comprising water and, optionally, a first surfactant, and, optionally, NaCl, to the first homogenizer; (iii) homogenizing the organic component with the inner aqueous component to form a primary emulsion; (iv) providing the primary emulsion to a second homogenizer at a first flow rate; (v) providing a continuous phase comprising water and a second surfactant to the second homogenizer at a second flow rate; (vi) homogenizing the primary emulsion and the continuous phase; and (vii) removing the solvent to form the polymer microspheres, wherein each of the formed polymer microspheres incorporates at least a portion of the inner aqueous component in the form of a plurality of emulsions. In some aspects, the polymer microspheres may be subjected to dehydration, in which case the polymer microspheres are characterized by a plurality of internal macrovoids.

In another aspect, a method for treating pain is provided. The method may comprise administering to a patient in need thereof a microsphere formulation, the microsphere formulation comprising: polymer microspheres, each polymer microsphere comprising: (i) an API comprising, consisting essentially of, or consisting of ketamine; and (ii) a biodegradable polymer comprising, consisting essentially of, or consisting of an acid end-capped PLA polymer or an acid end-capped PLGA polymer, wherein the biodegradable polymer has an IV of about 0.1 to about 0.3 dL/g. Each polymer microsphere may comprise a drug load of between about 20 wt/wt % to about 50 wt/wt %, and the polymer microspheres may have an average particle size of between about 30 μm to about 90 μm ($D_{50}$). In some aspects, the microsphere formulation is administered to the patient by intramuscular or subcutaneous injection with a dosing schedule of about every 1-3 days.

In another aspect, a method for treating pain is provided. The method may comprise administering by intramuscular or subcutaneous injection to a patient in need thereof a microsphere formulation made according to the methods described herein.

In another aspect, use is disclosed of a microsphere formulation comprising polymer microspheres, each polymer microsphere comprising: (i) an API comprising, consisting essentially of, or consisting of ketamine; and (ii) a biodegradable polymer comprising, consisting essentially of, or consisting of an acid end-capped PLA polymer or an acid end-capped PLGA polymer, wherein the biodegradable polymer has an IV of about 0.1 to about 0.3 dL/g, wherein each polymer microsphere may comprise a drug load of between about 20 wt/wt % to about 50 wt/wt %, and wherein the polymer microspheres may have an average particle size of between about 30 μm to about 90 μm ($D_{50}$), in the manufacture of a medicament for the treatment of pain.

In another aspect, a microsphere formulation comprising polymer microspheres, each polymer microsphere comprising: (i) an API comprising, consisting essentially of, or consisting of ketamine; and (ii) a biodegradable polymer comprising, consisting essentially of, or consisting of an acid end-capped PLA polymer or an acid end-capped PLGA polymer, wherein the biodegradable polymer has an IV of about 0.1 to about 0.3 dL/g, wherein each polymer microsphere may comprise a drug load of between about 20 wt/wt % to about 50 wt/wt %, and wherein the polymer microspheres may have an average particle size of between about 30 μm to about 90 μm ($D_{50}$), is provided for use as a medicament for the treatment of pain.

In another aspect, a kit is provided, the kit comprising: (i) an API comprising, consisting essentially of, or consisting of ketamine; and (ii) a biodegradable polymer comprising, consisting essentially of, or consisting of an acid end-capped PLA polymer or an acid end-capped PLGA polymer, wherein the biodegradable polymer has an IV of about 0.1 to about 0.3 dL/g, wherein each polymer microsphere may comprise a drug load of between about 20 wt/wt % to about 50 wt/wt %, and wherein the polymer microspheres may have an average particle size of between about 30 μm to about 90 μm ($D_{50}$). In some aspects, the kit further comprises a diluent for administration.

DETAILED DESCRIPTION

Figure 1:
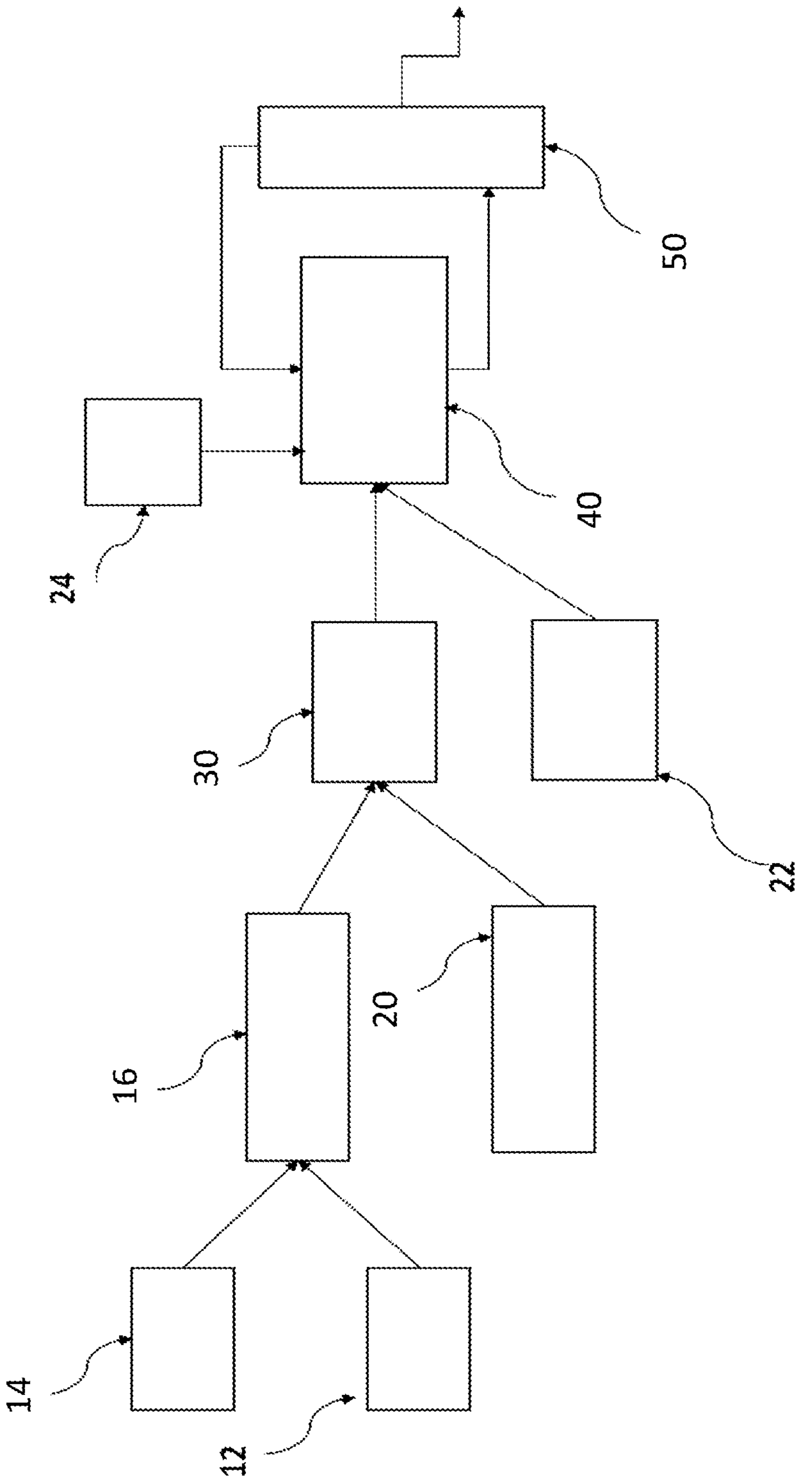
FIG. 1 is a flow chart illustrating an example method for making a double-emulsified microsphere formulation.

Microsphere formulations comprising ketamine are provided. The microsphere formulations comprise polymer microspheres, each polymer microsphere comprising: (i) an API comprising, consisting essentially of, or consisting of ketamine; and (ii) a biodegradable polymer comprising, consisting essentially of, or consisting of an acid end-capped PLA polymer or an acid end-capped PLGA polymer, wherein the biodegradable polymer has an IV of about 0.1 to about 0.3 dL/g. Each polymer microsphere may comprise a drug load of between about 20 wt/wt % to about 50 wt/wt %, and the polymer microspheres may have an average particle size of between about 30 μm to about 90 μm ($D_{50}$). In some aspects, the polymer microspheres are characterized by a plurality of internal emulsions, each emulsion comprising water and a surfactant. In some aspects, the polymer microspheres may be subjected to dehydration, in which case the polymer microspheres are characterized by a plurality of internal macrovoids.

In some aspects, the polymer microspheres are double emulsified. A method for making double emulsified polymer microspheres is provided, the method comprising: (i) contacting ketamine with a biodegradable PLA or PLGA polymer in the presence of a solvent to form an organic component and providing the organic component to a first homogenizer or a sonicator; (ii) providing an inner aqueous component comprising water and, optionally, a first surfactant, and, optionally, NaCl, to the first homogenizer or sonicator; (iii) homogenizing the organic component with the inner aqueous component to form a primary emulsion; (iv) providing the primary emulsion to a second homogenizer at a first flow rate; (v) providing a continuous phase comprising water and a second surfactant to the second homogenizer at a second flow rate; (vi) homogenizing the primary emulsion and the continuous phase; and (vii) removing the solvent to form the polymer microspheres, wherein each of the formed polymer microspheres incorporates at least a portion of the inner aqueous component in the form of a plurality of emulsions. In some aspects, the polymer microspheres may be subjected to dehydration, in which case the polymer microspheres are characterized by a plurality of internal macrovoids.

API—Ketamine

In some aspects, the ketamine comprises a racemic mixture. In some aspects, the ketamine may comprise the (S)-(+)-enantiomer ("esketamine") to the exclusion of the (R)-(−)-enantiomer ("arketamine"). Alternatively, the ketamine may comprise arketamine to the exclusion of esketamine.

In some aspects, the ketamine may comprise a pharmaceutically acceptable salt form or a free base form of any of ketamine, esketamine to the exclusion of arketamine, or arketamine to the exclusion of esketamine. Suitable salts may include hydrochloride, sulfate, acetate, phosphate, diphosphate, chloride, maleate, citrate, mesylate, nitrate, tartrate, gluconate, and the like. In other aspects, a complex salt may be used to decrease solubility, such as ketamine palmitate, ketamine benzoic acid, ketamine tosylic acid, ketamine camphor-sulfonic acid, and the like.

Unless otherwise noted, as used herein, the term "ketamine" is intended to include the racemic mixture as well as both of its individual enantiomers. In some aspects, the ketamine may be used in its racemic form. Alternatively, the ketamine may be used in its enantiomeric forms, such as in its "S" or "R" forms. An aspect may also include purified forms of the enantiomeric forms. For example, and without limitation, the "S" enantiomer to "R" enantiomer ratio may be from 51:49 up to 100:0 and every range included therein. Alternatively, the "R" enantiomer to "S" enantiomer ratio may be from 51:49 up to 100:0 and every range included therein. Each enantiomer may also exist in its (+) or (−) forms, such as in S(+) or S(−) forms. An alternative aspect is the use of a purified form of esketamine in which the ratio of S(+) to S(−) may be from 51:49 up to 100:0 and every range included therein. An alternate aspect is the use of a purified form of esketamine in which the ratio of S(−) to S(+) may be from 51:49 up to 100:0 and every range included there.

In one aspect, the API consists or consists essentially of (S)-ketamine base (esketamine base). In one aspect, the microsphere formulation is exclusive of hydromorphone.

Biodegradable Polymers

A PLA may be a suitable biodegradable polymer. In one aspect, the PLA may have an IV between about 0.1 to about 0.3 dL/g, including from about 0.13 to about 0.26 dL/g. In one aspect, the biodegradable polymer is an Ashland DL 02 A PLA polymer having an IV of about 0.13 dL/g. In one aspect, the biodegradable polymer is an Ashland DL 02 A PLA polymer having an IV of about 0.18 dL/g. In one aspect, the biodegradable polymer is an Ashland DL 02 A PLA polymer having an IV of about 0.26 dL/g. In one aspect, the biodegradable polymer is a mixture (e.g., a 1:1 mixture) of Ashland DL 02 A PLA polymers having an average IV of about 0.21 dL/g.

As the phrase is used herein, a "poly(lactide) polymer" is to be distinguished from and does not include a poly(lactic-co-glycolic acid) polymer. When a poly(lactic-co-glycolic acid) is intended, it will be explicitly recited. In certain, explicitly recited aspects, suitable biodegradable polymers may include poly(lactic-co-glycolic acid) ("PLGA") copolymers. In some aspects, the biodegradable polymer may comprise a PLGA copolymer having a co-monomer ratio for lactide to glycolide content of about 50:50 to about 85:15, including 75:25. In one aspect, the PLGA may have an IV between about 0.1 to about 0.3 dL/g, including about 0.18 dL/g. In one aspect, the biodegradable polymer comprises Resomer® RG 752 H, poly(D,L-lactide-co-glycolide), acid terminated, lactide:glycolide 75:25, manufactured by Evonik Rohm GmbH, having IV=0.18 dL/g ("752 H").

In some aspects, copolymers are specifically excluded. In one aspect, PLGA polymers are specifically excluded. In some aspects, PLGA polymers having a co-monomer ratio for lactide to glycolide content of about 50:50 are specifically excluded.

In some aspects, the biodegradable polymers are acid end-capped. In some aspects, ester end-capped biodegradable polymers are specifically excluded.

Dispersed Phase/Organic Component—Solvents

The ketamine and the polymer may be dissolved in a solvent mixture to form a dispersed phase (when using a single emulsion technique) or an organic component (when using a double emulsion technique). Suitable solvents may include methylene chloride (also known as dichloromethane or DCM), ethanol, ethyl acetate, acetic acid, acetone, acetonitrile, acetyl acetone, acrolein, acrylonitrile, allyl alcohol, 1,3-butanediol, 1,4-butanediol, 1-butanol, 2-butanol, tert-butanol, 2-butoxyethanol, n-butyl amine, butyl dioxitol acetate, butyraldehyde, butyric acid, 2-chloroethanol, diacetone alcohol, diacetyl, diethylamine, diethylene glycol diethyl ether, diethylene glycol dimethyl ether, diethylene glycol monobutyl ether, diethylene glycol monobutyl ether acetate, diethylene glycol monoethyl ether, diethylene glycol monoethyl ether acetate, diethylene glycol monomethyl ether, N,N-diethylnicotinamide, dimethyl sulfoxide, N,N-dimethylacetamide, N,N-dimethylformamide, 1,4-dioxane, 2-ethoxyethanol, 2-ethoxyethyl acetate, ethyl formate, ethylene glycol methyl ether acetate, formic acid, furfural, glycofurol, hexylene glycol, isobutanol, isopropyl alcohol, 2,6-lutidine, methyl acetate, methyl ethyl ketone, methyl isopropyl ketone, methyl propionate, N-methylpyrrolidone, morpholine, tert-pentanol, 2-picoline, 3-picoline, 4-picoline, piperidine, 1-propanol, propionaldehyde, propylene oxide, pyridine, pyrimidine, pyrrolidine, tetrahydrofuran, tetramethylurea, triacetin, triethylene glycol, trimethyl phosphate, and combinations thereof. In some aspects, the solvent comprises DCM, ethanol, ethyl acetate, or a combination of two or all of them. In some aspects, the solvent consists or consists essentially of a combination of DCM and ethanol. In some aspects, the solvent consists or consists essentially of an about 5:1 (by volume) ratio of DCM:ethanol.

Double Emulsified Polymer Microspheres—Inner Aqueous Component

In one aspect, the organic component is homogenized with an inner aqueous component to form a primary emulsion. In one aspect, the inner aqueous component comprises water. In one aspect, the inner aqueous component comprises water and a surfactant. In one aspect, the surfactant comprises polyvinyl alcohol ("PVA"). In some aspects, the inner aqueous component comprises PVA in an amount of about 0.35% to about 1.0% by weight in water. In some aspects, the inner aqueous component comprises PVA in an amount of about 0.35% by weight in water. In some aspects, the inner aqueous component comprises PVA in an amount of about 1.0% by weight in water. In one aspect, the inner aqueous component comprises NaCl. In one aspect, the inner aqueous component comprises up to 10 wt % NaCl, including about 0.5 wt %, about 1.0 wt %, about 1.5 wt %, about 2.0 wt %, about 2.5 wt %, about 3.0 wt %, about 3.5 wt %, about 4.0 wt %, about 4.5 wt %, about 5.0 wt %, about 5.5 wt %, about 6.0 wt %, about 6.5 wt %, about 7.0 wt %, about 7.5 wt %, about 8.0 wt %, about 8.5 wt %, about 9.0 wt %, and about 9.5 wt % NaCl. In one aspect, the inner aqueous component comprises between about 2.5 w % to about 5 wt % NaCl.

Figure 2A:
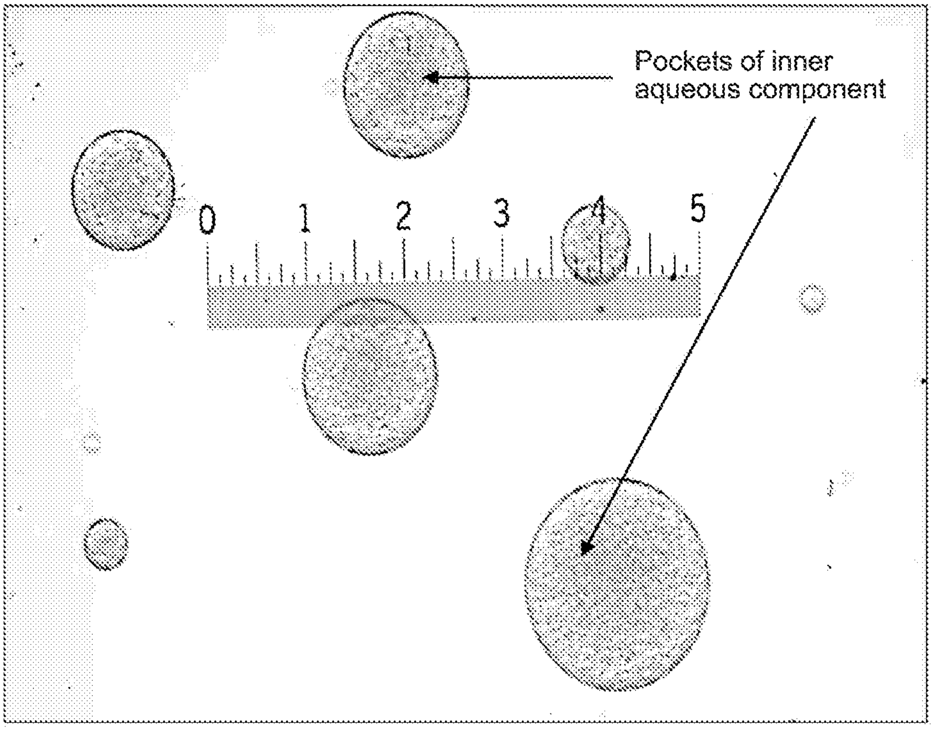
FIGS. 2A and 2B are two photographs showing a comparison between polymer microspheres prepared using a double emulsion technique (FIG. 2A) and a single emulsion technique (FIG. 2B), each prior to dehydration.
Figure 2B:
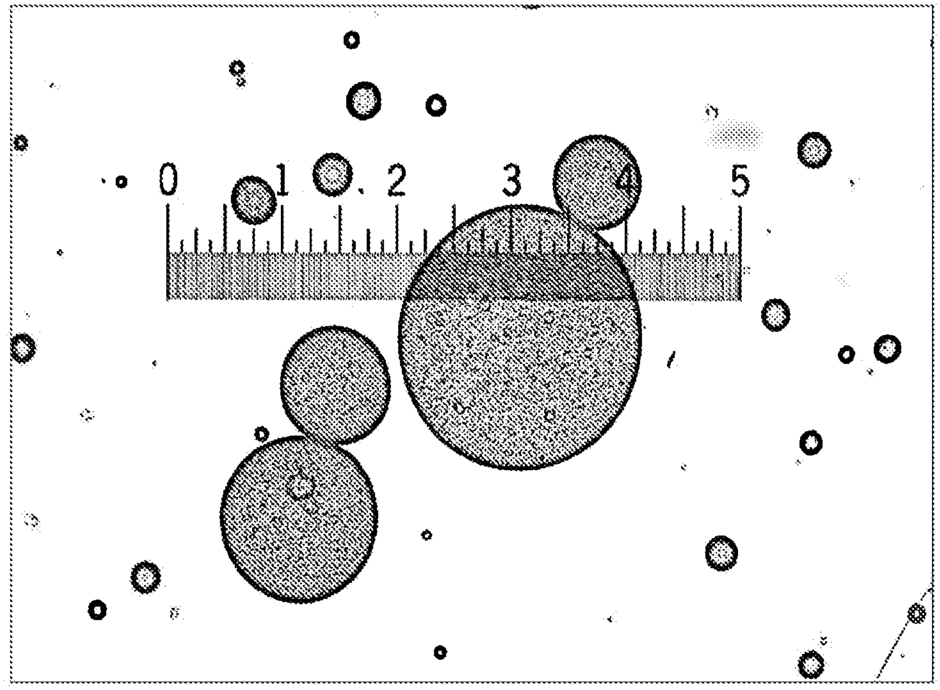

FIGS. 2A and 2B are two photographs showing a comparison between polymer microspheres prepared using a double emulsion technique (FIG. 2A) and a conventional single emulsion technique (FIG. 2B) (an example of each of which is described in U.S. Nonprovisional patent application Ser. No. 17/404,128, which is incorporated herein by reference in its entirety), each prior to dehydration. The double emulsified polymer microspheres are characterized in that each of the polymer microspheres incorporates a plurality of emulsions comprising water and the surfactant. In some aspects, the polymer microspheres may be subjected to dehydration, in which case the polymer microspheres are characterized by a plurality of internal macrovoids.

In one aspect, dehydration may be achieved by freeze drying, including by lyophilization or cryodesiccation, i.e., a low temperature dehydration process that involves freezing the polymer microspheres, lowering pressure, and removing the ice by sublimation. This is in contrast to dehydration methods that evaporate water using heat.

Continuous Phase

The dispersed phase or the primary emulsion may be homogenized with a continuous phase comprising water and, optionally, a surfactant, such as PVA, to form a secondary emulsion. The surfactant component may be present in the continuous phase in an amount of about 0.35% to about 1.0% by weight in water. In one aspect, the surfactant component comprises PVA in an amount of about 0.35% by weight in water. In one aspect, the surfactant component comprises PVA in an amount of about 1.0% by weight in water. The secondary emulsion may be subjected to solvent removal and washing processes to form the double emulsified polymer microspheres.

In some aspects, the dispersed phase/primary emulsion flow rate to the homogenizer may from about 10 mL/min to about 30 mL/min, including about 20 mL/min and about 25 mL/min. In some aspects, the continuous phase flow rate to the homogenizer may be about 2 L/min. Thus, in one aspect, the continuous phase:dispersed phase/primary emulsion ratio may be from about 66:1 to about 200:1, including about 100:1 and about 80:1.

The continuous phase may be provided at room temperature or above or below room temperature. In some aspects, the continuous phase may be provided at about 40° C., about 37° C., about 35° C., about 30° C., about 25° C., about 20° C., about 15° C., about 10° C., about 5° C., about 0° C., and any range or value between any of those values.

Homogenizer

In some aspects, the homogenization of the organic component and the inner aqueous component may be conducted in a high-speed homogenizer, e.g., in a T25 Ultra-turrax high-speed homogenizer operating, e.g., at 21,500 rpm for 30 seconds (e.g., run in 15 second intervals for two intervals) to form the primary emulsion. In other aspects, the homogenization of the organic component and the inner aqueous component may be conducted in a sonicator, e.g., a Q700 Sonicator (manufactured by Qsonica), or in a magic LAB® DISPAX-REACTOR® DR (manufactured by IKA).

In some aspects, the homogenization of the primary emulsion and the continuous phase may be conducted in an emulsifier or a homogenizer. For brevity, and because the methods are equally applicable to either, the phrase "homogenizer" contemplates a system or apparatus that can homogenize the primary emulsion and the continuous phase, emulsify the primary emulsion and the continuous phase, or both, which systems and apparatuses are known in the art. For example, in one aspect, the homogenizer is an in-line Silverson Homogenizer (commercially available from Silverson Machines, Waterside UK) or a Levitronix® BPS-i100 integrated pump system used, e.g., as described in U.S. Pat. No. 11,167,256, which is incorporated by reference herein in its entirety. In one aspect, the homogenizer is a membrane emulsifier. In one aspect, the homogenizer runs at an impeller speed of about 1,000 to about 4,000 revolutions per minute ("RPM"), including about 1,000 RPM, about 1,200 RPM, about 1,600 RPM, or about 2,500 RPM.

Average Particle Size

The polymer microspheres may be any size that is safely and efficaciously injectable by intramuscular or subcutaneous injection. In one aspect, the polymer microspheres may have an average particle size of less than 100 μm, or between about 30 μm and about 90 μm, including about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, and about 95 μm, and any range between such values.

Drug Load

The drug load of each polymer microsphere in a drug to polymer ratio, expressed as a percentage, may range from between about 20 wt/wt % to about 50 wt/wt %, including about 20 wt/wt %, about 25 wt/wt %, about 30 wt/wt %, about 35 wt/wt %, about 40 wt/wt %, about 45% wt/wt %, and about 50% wt/wt %, and any range between such values.

Release

The microsphere formulations are characterized in that they have an in vitro (under physiologically relevant conditions) and an in vivo duration of ketamine release of about 1-3 days.

Therapeutic Benefits

In one aspect, pain, including for example, post-operative pain, may be treated using the microsphere formulations, wherein the microsphere formulations are administered every about 1-3 days.

In another aspect, a method for treating pain is provided. The method may comprise administering to a patient in need thereof a microsphere formulation, the microsphere formulation comprising: polymer microspheres, each polymer microsphere comprising: (i) an API comprising, consisting essentially of, or consisting of ketamine; and (ii) a biodegradable polymer comprising, consisting essentially of, or consisting of an acid end-capped PLA polymer or an acid end-capped PLGA polymer, wherein the biodegradable polymer has an IV of about 0.1 to about 0.3 dL/g. Each polymer microsphere may comprise a drug load of between about 20 wt/wt % to about 50 wt/wt %, and the polymer microspheres may have an average particle size of between about 30 μm to about 90 μm ($D_{50}$). In some aspects, the microsphere formulation is administered to the patient by intramuscular or subcutaneous injection with a dosing schedule of about every one to three days.

In another aspect, a method for treating pain is provided. The method may comprise administering by intramuscular or subcutaneous injection to a patient in need thereof a microsphere formulation made according to the methods described herein.

In another aspect, use is disclosed of a microsphere formulation comprising polymer microspheres, each polymer microsphere comprising: (i) an API comprising, consisting essentially of, or consisting of ketamine; and (ii) a biodegradable polymer comprising, consisting essentially of, or consisting of an acid end-capped PLA polymer or an acid end-capped PLGA polymer, wherein the biodegradable polymer has an IV of about 0.1 to about 0.3 dL/g, wherein each polymer microsphere may comprise a drug load of between about 20 wt/wt % to about 50 wt/wt %, and wherein the polymer microspheres may have an average particle size of between about 30 μm to about 90 μm ($D_{50}$), in the manufacture of a medicament for the treatment of pain.

In another aspect, a microsphere formulation comprising polymer microspheres, each polymer microsphere comprising: (i) an API comprising, consisting essentially of, or consisting of ketamine; and (ii) a biodegradable polymer comprising, consisting essentially of, or consisting of an acid end-capped PLA polymer or an acid end-capped PLGA polymer, wherein the biodegradable polymer has an IV of about 0.1 to about 0.3 dL/g, wherein each polymer microsphere may comprise a drug load of between about 20 wt/wt % to about 50 wt/wt %, and wherein the polymer microspheres may have an average particle size of between about 30 μm to about 90 μm ($D_{50}$), is provided for use as a medicament for the treatment of pain.

In another aspect, a kit is provided, the kit comprising: (i) an API comprising, consisting essentially of, or consisting of ketamine; and (ii) a biodegradable polymer comprising, consisting essentially of, or consisting of an acid end-capped PLA polymer or an acid end-capped PLGA polymer, wherein the biodegradable polymer has an IV of about 0.1 to about 0.3 dL/g, wherein each polymer microsphere may comprise a drug load of between about 20 wt/wt % to about 50 wt/wt %, and wherein the polymer microspheres may have an average particle size of between about 30 μm to about 90 μm ($D_{50}$). In some aspects, the kit further comprises a diluent for administration.

The microsphere formulations are injectable formulations for administration via intramuscular or subcutaneous injection and not intrathecally. In some aspects, the intramuscularly or subcutaneously injectable formulation may further include sodium carboxymethylcellulose, tween 80, and mannitol.

EXAMPLES

Example 1—General Preparation of Microsphere Formulations Comprising Ketamine Via a Double Emulsion Method Microsphere Formation Phase. With reference to FIG. 1, an organic component 12 is formed by dissolving a biodegradable polymer (such as a PLA or a PLGA polymer) in an organic solvent (such as DCM, ethanol, or a combination thereof), followed by the addition of ketamine with mixing until completely dissolved. The organic component 12 is homogenized with an inner aqueous component ("IA component") 14 comprising water and, optionally, PVA, and, optionally, NaCl, in a high-speed homogenizer probe (such as a T25 Ultra-turrax, sonicator, or magic Lab® DISPAX-REACTOR®) 16 to form a primary emulsion ("PE") in place of DP 10. The PE is pumped into a homogenizer 30, such as an in-line Silverson Homogenizer or a Levitronix i100 (as described in U.S. Pat. No. 11,167,256), at a defined flow rate. The CP 20 comprising water and, optionally, PVA, is also pumped into the homogenizer 30 at a defined flow rate.

Microsphere Processing Phase. The formed or forming microspheres exit the homogenizer 30 and enter an SRV 40. Water 22 is added to the SRV 40 during microsphere formation to minimize the solvent level. The resulting suspension is mixed in the SRV 40 during the microsphere formation period. After the PE is exhausted, the CP and water flow additions are stopped, and the washing steps are initiated.

Solvent removal is achieved by washing the microspheres with room temperature water 24 (e.g., 25° C.) and hot water (35-39° C.) and filtering them through a hollow fiber filter 50 (commercially available as HFF from GE Healthcare). Excess solvent is removed and discarded, and the filtered microspheres are returned to the SRV until the desired level of solvent is removed from the microsphere formulation.

The washed microspheres are collected on a filter membrane and freeze-dried overnight in a lyophilizer (Virtis) to remove moisture. The resulting microspheres are a free-flowing off-white bulk powder.

Example 2—Preparation and Evaluation of an Ultra-Low Inherent Viscosity (0.18 dL/g) PLGA-Based Double Emulsion Microsphere Formulation Batch No. 1: The organic component was formed by dissolving 5.0 g of 752 H (IV=0.18 dL/g) in 24.5 g of DCM and 2.9 g of ethanol (5:1 ratio by volume), followed by the addition of esketamine (5.0 g) with mixing until completely dissolved. The organic component was homogenized with an IA component consisting of 1 mL of CP comprising water and 0.35% PVA in a T25 Ultra-turrax high-speed homogenizer operating at 21,500 rpm for 30 seconds to form the PE.

The PE was pumped into a Levitronix i100 (as described in U.S. Pat. No. 11,167,256) operating at 2,500 RPM at a rate of 25 mL/minute, along with a CP comprising water and 1.0% PVA, which was pumped at a rate of 2 L/min, for a CP:PE ratio of 80:1.

The formed or forming microspheres exited the homogenizer and entered an SRV. Deionized water was added to the SRV at 2 L/min. Solvent removal was achieved by washing the microspheres with ambient water (i.e., 25° C.) and hot water (35-39° C.) and filtering them through a hollow fiber filter.

The bulk suspension was collected via filtration and lyophilized to obtain a free-flowing powder with a yield of about 50%. The drug load was 22.8 wt/wt % (46% drug encapsulation efficiency based on a target drug load of 50 wt/wt %). The average particle size was 10 μm ($D_{10}$), 32 μm ($D_{50}$), 68 μm ($D_{90}$).

Figure 3:
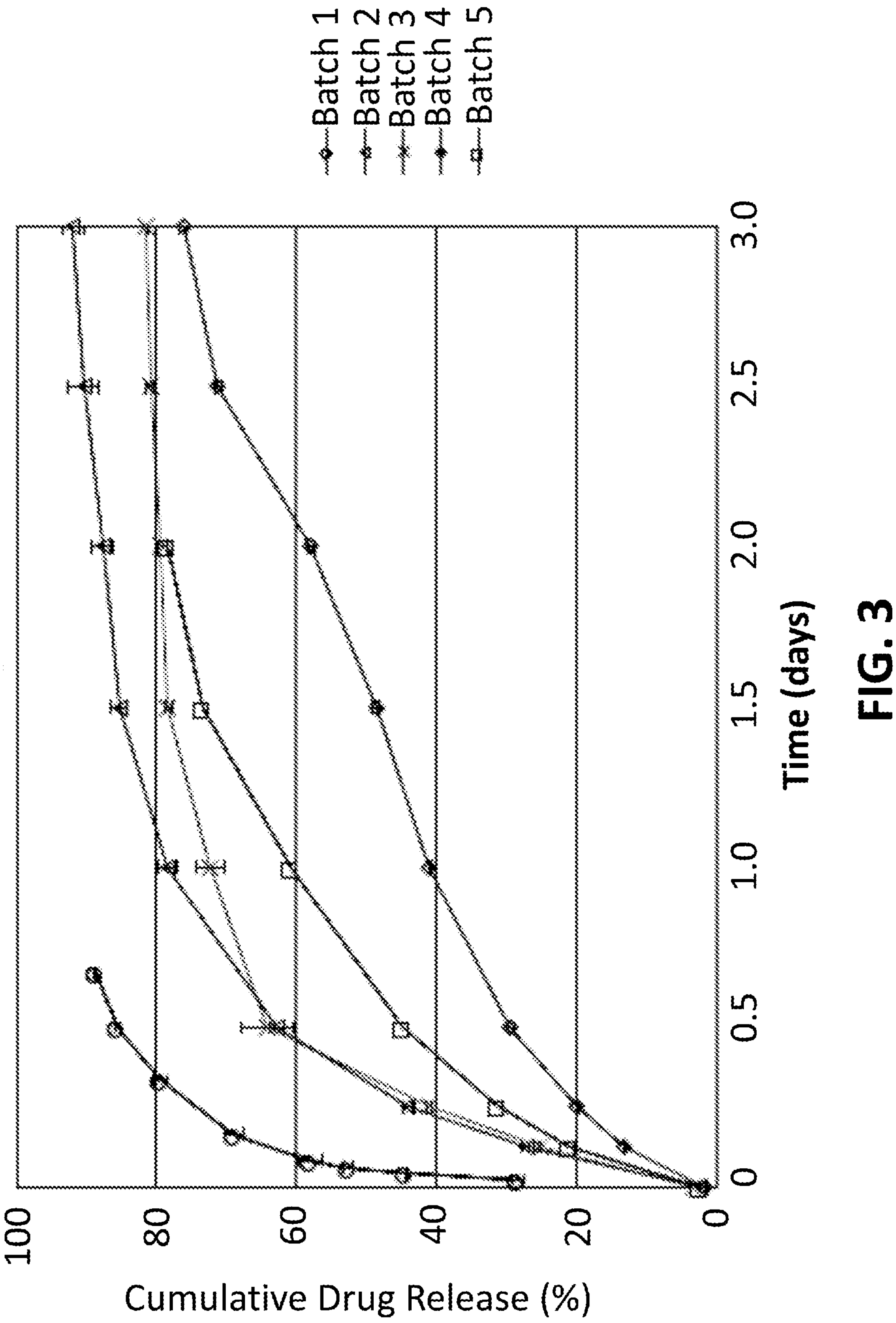
FIG. 3 is a graph showing an amount of ketamine released in vitro over time from several example double emulsified microsphere formulations (Batch Nos. 1-5).

Batch No. 1 was tested in an in vitro assay mimicking physiological conditions. The cumulative percent release of ketamine over time is shown graphically in FIG. 3.

Example 3—Preparation and Evaluation of an Ultra-Low Inherent Viscosity (0.18 dL/g) PLA-Based Double Emulsion Microsphere Formulation Batch No. 2: The organic component was formed by dissolving 6.0 g of DL 02 A (IV=0.18 dL/g) in 31.4 g of DCM and 3.7 g of ethanol (5:1 ratio by volume), followed by the addition of esketamine (4.0 g) with mixing until completely dissolved. The organic component was homogenized with an IA component consisting of 1 mL of CP comprising water and 0.35% PVA in a T25 Ultra-turrax high-speed homogenizer operating at 21,500 rpm for 30 seconds to form the PE.

The PE was pumped into a Levitronix i100 (as described in U.S. Pat. No. 11,167,256) operating at 1,600 RPM at a rate of 25 mL/minute, along with a CP comprising water and 1.0% PVA, which was pumped at a rate of 2 L/min, for a CP:PE ratio of 80:1.

The formed or forming microspheres exited the homogenizer and entered an SRV. Deionized water was added to the SRV at 2 L/min. Solvent removal was achieved by washing the microspheres with ambient water (i.e., 25° C.) and hot water (35-39° C.) and filtering them through a hollow fiber filter.

The bulk suspension was collected via filtration and lyophilized to obtain a free-flowing powder with a yield of about 67.1%. The drug load was 27.1 wt/wt % (67.8% drug encapsulation efficiency based on a target drug load of 40 wt/wt %). The average particle size was 24 μm ($D_{10}$), 52 μm ($D_{50}$), 96 μm ($D_{90}$).

Batch No. 2 was tested in an in vitro assay mimicking physiological conditions. The cumulative percent release of ketamine over time is shown graphically in FIG. 3.

Example 4—Preparation and Evaluation of an Ultra-Low Inherent Viscosity (0.18 dL/g) PLA-Based Double Emulsion Microsphere Formulation Batch No. 3: The organic component was formed by dissolving 6.0 g of DL 02 A (IV=0.18 dL/g) in 31.4 g of DCM and 3.7 g of ethanol (5:1 ratio by volume), followed by the addition of esketamine (4.0 g) with mixing until completely dissolved. The organic component was homogenized with an IA component consisting of 1 mL of CP comprising water and 0.35% PVA in a T25 Ultra-turrax high-speed homogenizer operating at 21,500 rpm for 30 seconds to form the PE.

The PE was pumped into a Levitronix i100 (as described in U.S. Pat. No. 11,167,256) operating at 1,200 RPM at a rate of 25 mL/minute, along with a CP comprising water and 1.0% PVA, which was pumped at a rate of 2 L/min, for a CP:PE ratio of 80:1.

The formed or forming microspheres exited the homogenizer and entered an SRV. Deionized water was added to the SRV at 2 L/min. Solvent removal was achieved by washing the microspheres with ambient water (i.e., 25° C.) and hot water (35-39° C.) and filtering them through a hollow fiber filter.

The bulk suspension was collected via filtration and lyophilized to obtain a free-flowing powder with a yield of about 65.5%. The drug load was 31.1 wt/wt % (77.8% drug encapsulation efficiency based on a target drug load of 40 wt/wt %). The average particle size was 28 μm ($D_{10}$), 63 μm ($D_{50}$), 111 μm ($D_{90}$).

Batch No. 3 was tested in an in vitro assay mimicking physiological conditions. The cumulative percent release of ketamine over time is shown graphically in FIG. 3.

Example 5—Preparation and Evaluation of an Ultra-Low Inherent Viscosity (0.26 dL/g) PLA-Based Double Emulsion Microsphere Formulation Batch No. 4: The organic component was formed by dissolving 6.0 g of DL 02 A (IV=0.26 dL/g) in 31.4 g of DCM and 3.7 g of ethanol (5:1 ratio by volume), followed by the addition of esketamine (4.0 g) with mixing until completely dissolved. The organic component was homogenized with an IA component consisting of 1 mL of CP comprising water and 0.35% PVA in a T25 Ultra-turrax high-speed homogenizer operating at 21,500 rpm for 30 seconds to form the PE.

The PE was pumped into a Levitronix i100 (as described in U.S. Pat. No. 11,167,256) operating at 1,600 RPM at a rate of 25 mL/minute, along with a CP comprising water and 1.0% PVA, which was pumped at a rate of 2 L/min, for a CP:PE ratio of 80:1.

The formed or forming microspheres exited the homogenizer and entered an SRV. Deionized water was added to the SRV at 2 L/min. Solvent removal was achieved by washing the microspheres with ambient water (i.e., 25° C.) and hot water (35-39° C.) and filtering them through a hollow fiber filter.

The bulk suspension was collected via filtration and lyophilized to obtain a free-flowing powder with a yield of about 67.0%. The drug load was 31.2 wt/wt % (78.0% drug encapsulation efficiency based on a target drug load of 40 wt/wt %). The average particle size was 27 μm (D10), 63 μm (D50), 111 μm (D90).

Batch No. 4 was tested in an in vitro assay mimicking physiological conditions. The cumulative percent release of ketamine over time is shown graphically in FIG. 3.

Example 6—Preparation and Evaluation of a 1:1 Combination of Ultra-Low Inherent Viscosity (Average 0.21 dL/g) PLAs in a Double Emulsion Microsphere Formulation Batch No. 5: The organic component was formed by dissolving a 1:1 combination of 3.0 g of a first DL 02 A (IV=0.16 dL/g) and 3.0 g of a second DL 02 A (IV=0.26 dL/g) in 31.4 g of DCM and 3.7 g of ethanol (5:1 ratio by volume), followed by the addition of esketamine (4.0 g) with mixing until completely dissolved. The organic component was homogenized with an IA component consisting of 1 mL of CP comprising water and 0.35% PVA in a T25 Ultra-turrax high-speed homogenizer operating at 21,500 rpm for 30 seconds to form the PE.

The PE was pumped into a Levitronix i100 (as described in U.S. Pat. No. 11,167,256) operating at 1,600 RPM at a rate of 25 mL/minute, along with a CP comprising water and 1.0% PVA, which was pumped at a rate of 2 L/min, for a CP:PE ratio of 80:1.

The formed or forming microspheres exited the homogenizer and entered an SRV. Deionized water was added to the SRV at 2 L/min. Solvent removal was achieved by washing the microspheres with ambient water (i.e., 25° C.) and hot water (35-39° C.) and filtering them through a hollow fiber filter.

The bulk suspension was collected via filtration and lyophilized to obtain a free-flowing powder with a yield of about 66.7%. The drug load was 30.7 wt/wt % (76.8% drug encapsulation efficiency based on a target drug load of 40 wt/wt %). The average particle size was 20 μm (D10), 53 μm (D50), 93 μm (D90).

Batch No. 5 was tested in an in vitro assay mimicking physiological conditions. The cumulative percent release of ketamine over time is shown graphically in FIG. 3.

Example 7—Preparation and Evaluation of an Ultra-Low Inherent Viscosity (average 0.13 dL/g) PLA in a Double Emulsion Microsphere Formulation, Including NaCl in the Inner Aqueous Component Batch No. 6: The organic component was formed by dissolving 6.0 g of DL 02 A (IV=0.13 dL/g) (MW=10.4 kDa) in 31.4 g of DCM and 3.7 g of ethanol (5:1 ratio by volume), followed by the addition of esketamine (4.0 g) with mixing until completely dissolved. The organic component was homogenized with an IA component consisting of 1 mL of CP comprising water and 5% NaCl in 0.35% PVA in a T25 Ultra-turrax high-speed homogenizer operating at 21,500 rpm for 30 seconds to form the PE.

The PE was pumped into a Levitronix i100 (as described in U.S. Pat. No. 11,167,256) operating at 1,000 RPM at a rate of 25 mL/minute, along with a CP comprising water and 1.0% PVA, which was pumped at a rate of 2 L/min, for a CP:PE ratio of 80:1.

The formed or forming microspheres exited the homogenizer and entered an SRV. Deionized water was added to the SRV at 2 L/min. Solvent removal was achieved by washing the microspheres with room temperature water (e.g., 25° C.) and hot water (35-39° C.) and filtering them through a hollow fiber filter.

The bulk suspension was collected via filtration and lyophilized to obtain a free-flowing powder with a yield of about 62%. The drug load was 26.6 wt/wt % (66.5% drug encapsulation efficiency based on a target drug load of 40 wt/wt %). The average particle size was 17 μm (D10), 46 μm (D50), 85 μm (D90). The microsphere molecular weight was 10.4 kDa.

Figure 4:
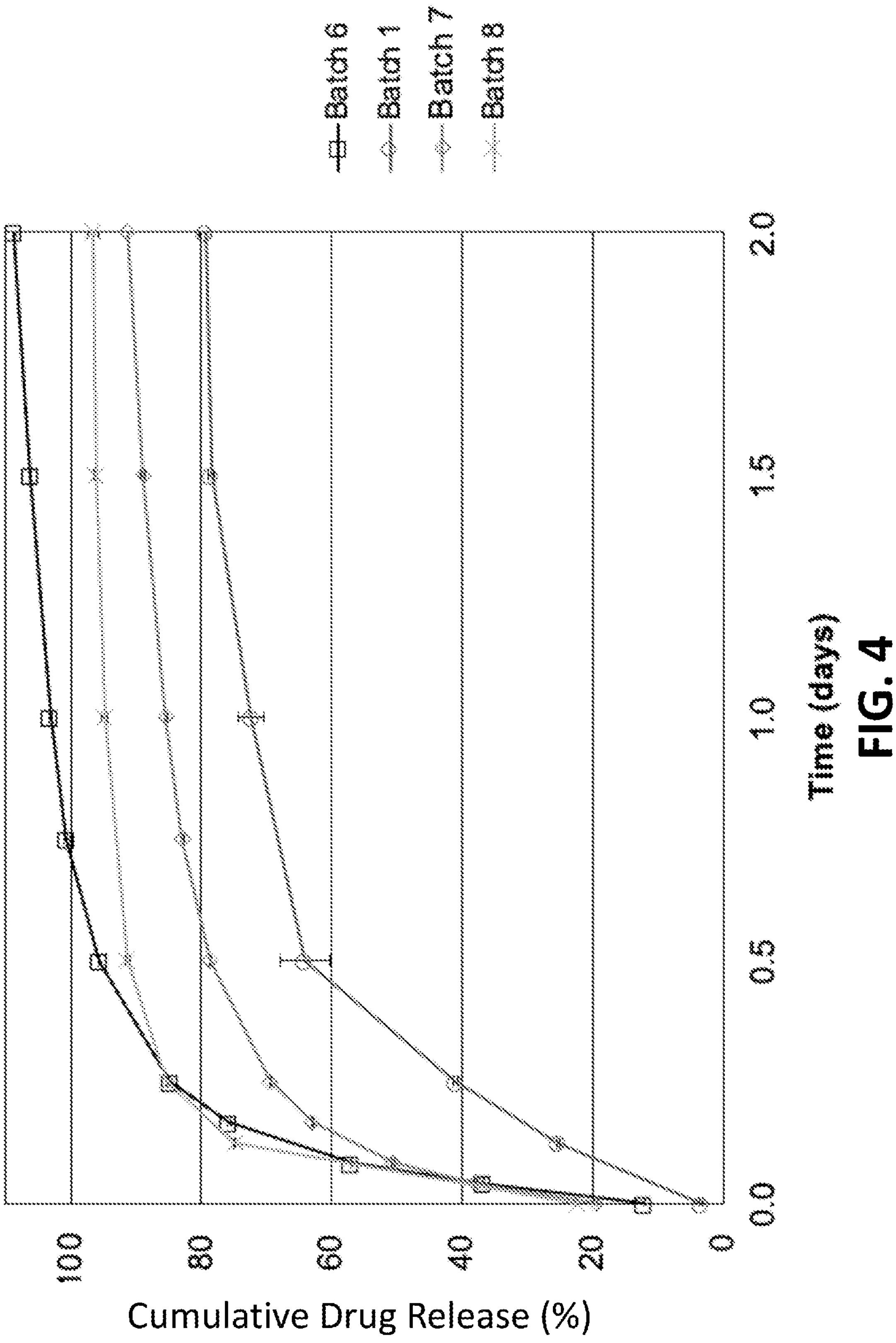
FIG. 4 is a graph showing an amount of ketamine released in vitro over time from several example double emulsified microsphere formulations that included NaCl in the inner aqueous component during preparation (Batch Nos. 6-8) compared to one double emulsified microsphere formulation that did not include NaCl in the inner aqueous component during preparation (Batch No. 1).

Batch No. 6 was tested in an in vitro assay mimicking physiological conditions. The cumulative percent release of ketamine over time is shown graphically in FIG. 4.

Example 8—Preparation and Evaluation of an Ultra-Low Inherent Viscosity (Average 0.13 dL/g) PLA in a Double Emulsion Microsphere Formulation, Including NaCl in the Inner Aqueous Component Batch No. 7: The organic component was formed by dissolving 6.0 g of DL 02 A (IV=0.13 dL/g) (MW=10.9 kDa) in 31.4 g of DCM and 3.7 g of ethanol (5:1 ratio by volume), followed by the addition of esketamine (4.0 g) with mixing until completely dissolved. The organic component was homogenized with an IA component consisting of 1 mL of CP comprising water and 2.5% NaCl in 0.35% PVA in a T25 Ultra-turrax high-speed homogenizer operating at 21,500 rpm for 30 seconds to form the PE.

The PE was pumped into a Levitronix i100 (as described in U.S. Pat. No. 11,167,256) operating at 1,000 RPM at a rate of 25 mL/minute, along with a CP comprising water and 1.0% PVA, which was pumped at a rate of 2 L/min, for a CP:PE ratio of 80:1.

The formed or forming microspheres exited the homogenizer and entered an SRV. Deionized water was added to the SRV at 2 L/min. Solvent removal was achieved by washing the microspheres with ambient water (i.e., 25° C.) and hot water (35-39° C.) and filtering them through a hollow fiber filter.

The bulk suspension was collected via filtration and lyophilized to obtain a free-flowing powder with a yield of about 66%. The drug load was 25.6 wt/wt % (64.0% drug encapsulation efficiency based on a target drug load of 40 wt/wt %). The average particle size was 35 μm (D10), 78 μm (D50), 132 μm (D90). The microsphere molecular weight was 10.3 kDa.

Batch No. 7 was tested in an in vitro assay mimicking physiological conditions. The cumulative percent release of ketamine over time is shown graphically in FIG. 4.

Example 9—Preparation and Evaluation of an Ultra-Low Inherent Viscosity (Average 0.13 dL/g) PLA in a Double Emulsion Microsphere Formulation, Including NaCl in the Inner Aqueous Component Batch No. 8: The organic component was formed by dissolving 6.0 g of DL 02 A (IV=0.13 dL/g) (MW=10.9) in 17.9 g of DCM and 2.1 g of ethanol (5:1 ratio by volume), followed by the addition of esketamine (4.0 g) with mixing until completely dissolved. The organic component was homogenized with an IA component consisting of 1 mL of CP comprising water and 2.5% NaCl in 0.35% PVA in a T25 Ultra-turrax high-speed homogenizer operating at 21,500 rpm for 30 seconds to form the PE.

The PE was pumped into a Levitronix i100 (as described in U.S. Pat. No. 11,167,256) operating at 1,000 RPM at a rate of 25 mL/minute, along with a CP comprising water and 1.0% PVA, which was pumped at a rate of 2 L/min, for a CP:PE ratio of 80:1.

The formed or forming microspheres exited the homogenizer and entered an SRV. Deionized water was added to the SRV at 2 L/min. Solvent removal was achieved by washing the microspheres with ambient water (i.e., 25° C.) and hot water (35-39° C.) and filtering them through a hollow fiber filter.

The bulk suspension was collected via filtration and lyophilized to obtain a free-flowing powder with a yield of about 53.6%. The drug load was 28.5 wt/wt % (71.3% drug encapsulation efficiency based on a target drug load of 40 wt/wt %). The average particle size was 11 μm (D10), 88 μm (D50), 172 μm (D90). The microsphere molecular weight was 10.4 kDa.

Batch No. 8 was tested in an in vitro assay mimicking physiological conditions. The cumulative percent release of ketamine over time is shown graphically in FIG. 4.

The aspects disclosed herein are not intended to be exhaustive or to be limiting. A skilled artisan would acknowledge that other aspects or modifications to instant aspects can be made without departing from the spirit or scope of the invention. The aspects of the present disclosure, as generally described herein and illustrated in the figures, can be arranged, substituted, combined, separated, and designed in a wide variety of different configurations, all of which are contemplated herein.

Unless otherwise specified, "a," "an," "the," "one or more of," and "at least one" are used interchangeably. The singular forms "a", "an," and "the" are inclusive of their plural forms. The recitations of numerical ranges by endpoints include all numbers subsumed within that range (e.g., 1 to 5 includes 1, 1.5, 2, 2.75, 3, 3.80, 4, 5, etc.). The terms "comprising" and "including" are intended to be equivalent and open-ended. The phrase "consisting essentially of" means that the composition or method may include additional ingredients and/or steps, but only if the additional ingredients and/or steps do not materially alter the basic and novel characteristics of the claimed composition or method. The phrase "selected from the group consisting of" is meant to include mixtures of the listed group.

When reference is made to the term "each," it is not meant to mean "each and every, without exception." For example, if reference is made to microsphere formulation comprising polymer microspheres, and "each polymer microsphere" is said to have a particular ketamine content, if there are 10 polymer microspheres, and two or more of the polymer microspheres have the particular ketamine content, then that subset of two or more polymer microspheres is intended to meet the limitation.

The term "about" in conjunction with a number is simply shorthand and is intended to include ±10% of the number. This is true whether "about" is modifying a stand-alone number or modifying a number at either or both ends of a range of numbers. In other words, "about 10" means from 9 to 11. Likewise, "about 10 to about 20" contemplates 9 to 22 and 11 to 18. In the absence of the term "about," the exact number is intended. In other words, "10" means 10.

What is claimed is:

1. A microsphere formulation, comprising:

polymer microspheres, each polymer microsphere comprising:

(i) an active pharmaceutical ingredient consisting essentially of ketamine or esketamine; and (ii) a biodegradable polymer consisting essentially of an acid end-capped poly(lactide) (PLA) polymer, having an inherent viscosity (IV) of about 0.1 to about 0.3 dL/g, wherein each polymer microsphere has a ketamine or esketamine drug load of between about 20 wt/wt % to about 50 wt/wt %, and wherein the polymer microspheres have a particle size of between about 30 μm to about 90 μm ($D_{50}$), and wherein the polymer microspheres are characterized in that each of the polymer microspheres comprises an internal polymer phase, and a plurality of internal macrovoids dispersed within the internal polymer phase; and wherein the polymer microspheres are prepared by a method comprising:

(1) contacting the ketamine with the PLA polymer in the presence of a solvent to form an organic component;

(2) emulsifying an inner aqueous component consisting essentially of water, polyvinyl alcohol, and NaCl with the organic component to form a primary emulsion;

(3) emulsifying the primary emulsion with a continuous phase comprising water to form a secondary emulsion;

(4) removing the solvent from the secondary emulsion to form the polymer microspheres; and (5) subjecting the polymer microspheres to dehydration.

2. The microsphere formulation of claim 1, wherein the active pharmaceutical ingredient consists essentially of esketamine.

3. The microsphere formulation of claim 1, wherein each polymer microsphere has a ketamine or esketamine drug load of between about 20 wt/wt % to about 30 wt/wt %.

4. The microsphere formulation of claim 1, wherein the polymer microspheres have a particle size of between about 45 μm about 90 μm ($D_{50}$).

5. The microsphere formulation of claim 1, wherein the PLA polymer has an IV of between about 0.13 dL/g and 0.26 dL/g.

6. The microsphere formulation of claim 1, wherein each polymer microsphere has a ketamine or esketamine drug load of between about 25 wt/wt % to about 35 wt/wt %.

7. The microsphere formulation of claim 1, wherein each of the polymer microsphere has a ketamine or esketamine drug load of between about 25 wt/wt % to about 30 wt/wt %, and wherein the polymer microspheres have a particle size of between about 45 μm about 90 μm ($D_{50}$).

8. A kit, the kit comprising: (i) the microsphere formulation of claim 1; and (ii) a diluent for administration.

9. A pharmaceutical composition comprising the microsphere formulation of claim 1.

10. The microsphere formulation of claim 1, wherein each of the polymer microspheres is further characterized in that the ketamine or esketamine is dispersed within the internal polymer phase.

* * * * *